United States Patent [19]

Birchall

[11] Patent Number: 5,814,347
[45] Date of Patent: Sep. 29, 1998

[54] THERAPEUTIC COMPOSITIONS CONTAINING A LITHIUM COMPOUND AND SILICA

[75] Inventor: James Derek Birchall, Mouldsworth, Great Britain

[73] Assignee: Keele University, Staffordshire, United Kingdom

[21] Appl. No.: 522,265

[22] PCT Filed: Mar. 11, 1994

[86] PCT No.: PCT/GB94/00484

§ 371 Date: Nov. 6, 1995

§ 102(e) Date: Nov. 6, 1995

[87] PCT Pub. No.: WO94/20119

PCT Pub. Date: Sep. 15, 1994

[30] Foreign Application Priority Data

Mar. 12, 1993 [GB] United Kingdom ............... 9305040
Nov. 26, 1993 [GB] United Kingdom ............... 9324360

[51] Int. Cl.$^6$ .................................................. A61K 33/14
[52] U.S. Cl. ............................................................ 424/677
[58] Field of Search ............................................. 424/677

[56] References Cited

U.S. PATENT DOCUMENTS 3,639,625  2/1972  Sherwin .

FOREIGN PATENT DOCUMENTS 0135312  3/1985  European Pat. Off. .
2182913  12/1973  France .

OTHER PUBLICATIONS

Martindale, The Extra Pharmacopoeia, Thirteenth Edition, London, The Pharmaceutical Press, 1993, p. 1221, col. 2, lines 32–38.

Buchan, A.; Randall, S.; Hartley, C.E.; Skinner, G.R.B.; and Fuller, A; Effect of lithium salts on the replication of viruses and non–viral microorganisms; Lithium: Inorganic Pharmacology and Psychiatric Use, Proceedings of the 2nd British Lithium Congress held at Wolverhampton Polytechnic, Sep. 6–9, 1987.

ABEQ US 5223271 A. UPAB, 93. Nov. 16.

Chemical Abstracts 107:12 1107 (1985). Biener.

*Primary Examiner*—Zohreh Fay
*Attorney, Agent, or Firm*—Clifford W. Browning; Woodard, Emhardt, Naughton Moriarty & McNett

[57] ABSTRACT

A therapeutic composition for the treatment of virus-induced cutaneous infections comprises a first material for blocking viral DNA replication and a second finely divided material which absorbs exudated fluid from vesicles. Preferred compositions comprise a lithium compound (as the material for blocking viral DNA replication) and silica (as the material for absorbing exudated fluid from vesicles). An example of composition in accordance with the invention comprises a lithium compound dissolved or suspended in an aqueous silica salt.

16 Claims, No Drawings ved infec-
THERAPEUTIC COMPOSITIONS CONTAINING A LITHIUM COMPOUND AND SILICA

The present invention relates to therapeutic compositions for use in the treatment of virus-induced cutaneous infections.

BACKGROUND OF THE INVENTION

A number of viral infections give rise to cutaneous lesions which can be painful, persistent and resistant to treatment. Complete healing requires the inhibition of viral replication and the regrowth of cutaneous tissue without scar formation. Examples of such viral infections include those produced by herpes virus—the most widely distributed viruses in human beings with some estimates suggesting that 60% of the population are affected. Infection with this virus remains sub-clinical and symbiotic in the cells of the host. However, this can be disturbed by intercurrent infections (e.g. the common cold and even, in some subjects, exposure to sunlight). There then develop typical herpetic vesicles especially around the mucocutaneous junction of lips and face. The genitals may be infected, the exudation from cutaneous lesions being especially infective and containing the virus in large amounts. A serious complication of cutaneous lesions is ocular involvement since this may lead to dendritic ulceration with scarring and impairment of vision. Zoster is also a virally induced lesion in which infective vesicles form.

SUMMARY OF THE INVENTION

According to a first aspect of the present invention there is provided a therapeutic composition for the treatment of virus-induced cutaneous infections, the composition comprising a first material for blocking viral DNA replication and a second finely divided material which absorbs exudated fluid from vesicles.

According to a second aspect of the present invention there is provided the use of a first material for blocking viral DNA replication and a second finely divided material which absorbs exudated fluid from vesicles for the manufacture of a medicament for the treatment of virus-induced cutaneous infections.

The preparations of the present invention, when applied to cutaneous lesions, have three co-operative effects:

(a) they absorb and immobilize the virus-containing infectious exudation from vesicles, restricting spreading, (b) they block viral DNA replication, (c) they promote epithelialization and rapid healing without scarring.

The material for blocking DNA replication may be an organic or inorganic compound known to possess this function. Most preferably the material is a lithium salt (with an organic or inorganic acid) since such materials are simple and free from side effects. Examples of suitable lithium salts are halide salts (particularly chloride, bromide and iodide) as well as the acetate, lactate, and succinate salts. Further more, lithium salts with polymeric anions (e.g. such as based on alginic acid or carboxymethyl cellulose) may be used. Organic materials which may be used include 5-iodo-2'-deoxyuridine and may if desired be used in conjunction with a lithium salt.

The material for absorbing exudated fluid from vesicles may for example be calcium carbonate, talc or a clay. It is however more preferred that the material is silica or a silicate. These latter materials are highly absorptive and immobilise absorbed exudate.

As mentioned above the second material for absorbing exudated fluid is used in finely divided form, preferably having a surface area of at least $1 \text{ m}^2\text{g}^{-1}$ more preferably at least $100 \text{ m}^2\text{g}^{-1}$. The average particle size of the material is preferably less than 30 microns, more preferably less than 10 microns, and most preferably less than 1 micron (e.g. colloidal size).

A preparation in accordance with the first aspect of the invention may, for example, comprise up to 60% by weight of the material for absorbing exudate. The amount by weight of the material for blocking viral DNA replication will generally (but not necessarily) be less than that of the exudate absorbing material and will typically (but again not necessarily) be less than 5% by weight, e.g. less than 1% by weight. The composition will generally also incorporate a pharmaceutically acceptable vehicle, e.g. water.

DESCRIPTION OF THE PREFERRED EMBODIMENTS

Preferred compositions in accordance with the invention comprise silica and a compound of lithium. Silica ($SiO_2 \cdot nH_2O$) of small particle size and high surface area (preferably, greater than $200 \text{ m}^2\text{g}^{-1}$) is found to promote the healing of skin lesions with rapid epithelialization. Colloidal silica is preferred in the preparation. When applied cutaneously, a suspension of colloidal silica leaves a deposit of the high surface area solid material. This absorbs any exudated fluid from vesicles, preventing spreading and thus extended infection.

The silica and lithium compound act synergistically in resolving virally-induced cutaneous lesions produced by herpes, pox and adenovirus. There is evidence that the incidence of recurrent outbreak of skin lesions is reduced following the application of this preparation.

The best effects in terms of the rapid resolution of herpes-induced cutaneous lesions are produced by preparations made by dissolving or suspending a lithium compound in an aqueous colloidal silica sol. The silica sol may be prepared by any of the methods known in the art including the acidification of an alkali silicate solution (especial lithium silicate solution), the hydrolysis of alkoxysilane (e.g. tetraethoxysilane), the cation-exchange of an alkalisilicate solution etc. Such methods are described in The Chemistry of Silica by R. K. Iler, Wiley 1979.

The particle size of the suspended silica in such suspensions is preferably less than $1 \mu m$ and preferably of the order of $200 \text{ Å}$ thus providing a high, absorbent surface area. The suspension can contain from <1% to >30% w/w $SiO_2$ in an aqueous base. Colloidal sols can also be produced by the hydrolysis of trialkoxysilane in which case the corresponding alcohol (preferably ethyl alcohol) may remain in the liquid phase of the preparation. Silica sols are sold commercially and these may be used.

The lithium compound is either dissolved or suspended as fine particles in the liquid phase of the preparation. Lithium chloride, for example, may be dissolved in the aqueous phase of a silica sol. Compounds of low solubility may be comminuted in the silica suspension by co-grinding or colloid milling. The amount of lithium thus homogeneously incorporated may range from 0.1 mM upwards and is preferably in the range 50 mM-5M. Amounts above this upper limit may be used but without any marked advantage.

Typically the amount used will be in the range 50 mM to 500 mM.

It is also possible to formulate preparations of the invention as ointments which may for example contain up to 60% by weight silica.

A typical preparation which was used in trials was made as follows. A silica sol was prepared by the acidification and dialysis of sodium silicate solution and containing 2.5 gram $SiO_2$ per 100 ml. The particle size of the $SiO_2$ particles averaged 250 Å. To this sol was added 100 mM of lithium lactate as a powder. This was incorporated homogeneously by milling.

The preparation was used in the treatment of herpes simplex in particularly vulnerable subjects by free topical application by the patient. The results were followed closely and evaluated in terms of:

(a) suppression of vesicle formation when applied at the first sign of irritation (b) resolution of existing vesicles when applied after their emergence, (c) relief of inflammation, irritation and pain, (d) full resolution of skin lesions with no scarring.

It was found that application of the preparation at the earliest stages of irritation, prevented vesicle eruption and cutaneous lesions did not appear.

When applied to existing and exuding vesicles, these dried rapidly and pain was eliminated and this was followed by complete healing within a much shorter period than normally experienced by the patient.

Preparation such as those described containing silica and lithium as essential ingredients may also optionally contain viscosity modifiers, colouring agents, emollients, bacteriostatic and antiseptic agents, analgesics and known agents for the treatment of virally-induced cutaneous lesions. They may be presented as pastes, creams and liquid sols. An effective preparation (although less popular with patients) is a powder prepared by impregnating a finely divided silica powder, preferably a silica prepared by precipitation and drying or by the gas phase oxidation of $SiCl_4$ etc, and of high surface area (>200 $m^2g^{-1}$), with a solution or suspension of a lithium salt.

I claim:

1. A therapeutic composition for the treatment of virus-induced cutaneous infections, the composition comprising a lithium salt for blocking viral DNA replication and finely divided silica or a finely divided silicate which absorbs exudated fluid from vesicles.

2. A composition as claimed in claim 1 wherein the lithium salt is a lithium halide.

3. A composition as claimed in claim 1 wherein the lithium salt is the acetate, lactate, or succinate salt.

4. A composition as claimed in claim 1 wherein the lithium salt comprises a polymeric anion.

5. A composition as claimed in claim 1 wherein the silica or silicate has a surface area of at least 100 $m^2g^{-1}$.

6. A composition as claimed in claim 1 wherein the silica or silicate has a particle size less than 30 microns.

7. A composition as claimed in claim 6 wherein the silica or silicate has a particle size less than 10 microns.

8. A composition as claimed in claim 7 wherein the silica or silicate has a particle size less than 1 micron.

9. A composition as claimed in claim 1 comprising less than 5% by weight of the lithium salt.

10. A composition as claimed in claim 9 comprising less than 1% by weight of the lithium salt.

11. A composition as claimed in claim 1 comprising up to 60% by weight of silica or silicate.

12. A composition as claimed in claim 1 which comprises a solution or suspension of a lithium salt in an aqueous colloidal silica sol.

13. A composition as claimed in claim 12 containing from 1% to 30% by weight of silica.

14. A composition as claimed in claim 12 containing at least 0.1 mM of the lithium compound.

15. A composition as claimed in claim 14 containing 50 mM–5M of the lithium compound.

16. A method of treating virus-induced cutaneous infections comprising applying to the infection a composition containing:

(i) a lithium salt for blocking viral DNA replication; and (ii) finely divided silicate, which absorbs fluid exudated from vesicles.

* * * * *

UNITED STATES PATENT AND TRADEMARK OFFICE
CERTIFICATE OF CORRECTION

PATENT NO : 5,814,347

DATED : September 29, 1998

INVENTOR(S) : BIRCHALL, James Derek

It is certified that error appears in the above-identified patent and that said Letters Patent is hereby corrected as shown below:

In column 2, line 42, please change "especail" to --especially--.

In column 2, line 52, please change "trialkoxysilane" to --tetralkoxysilane--.

Signed and Sealed this

Twenty-third Day of February, 1999

Attest:

Q. TODD DICKINSON

Attesting Officer     Acting Commissioner of Patents and Trademarks